United States Patent [19]

Riebel et al.

[11] Patent Number: 4,665,061
[45] Date of Patent: May 12, 1987

[54] CERTAIN (O-PYRID-2-YL)-5-TRIFLUORMETHYL PHOSPHORIC, THIOPHOSPHORIC, DITHIOPHOSPHORIC, PHOSPHORAMIDIC, THIOPHOSPHORAMIDIC ESTERS HAVING INSECTICIDAL OR NEMATOCIDAL PROPERTIES

[75] Inventors: Hans-Jochem Riebel, Wuppertal; Bernhard Homeyer, Leverkusen; Benedikt Becker, Mettmann; Wolfgang Behrenz, Overath, all of Fed. Rep. of Germany

[73] Assignee: Bayer Aktiengesellschaft, Leverkusen, Fed. Rep. of Germany

[21] Appl. No.: 743,456

[22] Filed: Jun. 11, 1985

[30] Foreign Application Priority Data

Jun. 27, 1984 [DE] Fed. Rep. of Germany ....... 3423639

[51] Int. Cl.$^4$ .......................... C07F 9/58; A01N 57/16
[52] U.S. Cl. .......................................... 514/89; 546/25
[58] Field of Search ............................. 546/25; 514/89

[56] References Cited

U.S. PATENT DOCUMENTS

| | | | |
|---|---|---|---|
| 3,244,586 | 4/1966 | Rigterink | 546/25 |
| 3,743,648 | 7/1973 | Rigterink | 546/25 |
| 3,810,902 | 5/1974 | Rigterink | 546/25 |
| 4,320,122 | 3/1982 | Theobald et al. | 514/89 |

*Primary Examiner*—Alan L. Rotman
*Attorney, Agent, or Firm*—Sprung Horn Kramer & Woods

[57] ABSTRACT

A phosphoric acid ester of the formula

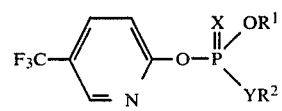

in which
Y is oxygen, sulphur or —NR—,
R is hydrogen or alkyl,
X is oxygen or sulphur, and
$R^1$ and $R^2$ each independently is alkyl.

11 Claims, No Drawings

CERTAIN (O-PYRID-2-YL)-5-TRIFLUORMETHYL PHOSPHORIC, THIOPHOSPHORIC, DITHIOPHOSPHORIC, PHOSPHORAMIDIC, THIOPHOSPHORAMIDIC ESTHERS HAVING INSECTICIDAL OR NEMATOCIDAL PROPERTIES

The invention relates to new phosphoric acid esters, a process for their preparation and their use as agents for combating pests, in particular as insecticides and nematicides.

It is known that certain O-pyridyl(thiono)phosphates, such as, for example, O,O-diethyl O-(3,5-dichloropyrid-2-yl)phosphate and O,O-diethyl O-(3,5-dichloropyrid-2-yl)thionophosphate, have a pesticidal action (compare U.S. Pat. No. 3,244,586). However, the action of these known compounds is not always completely satisfactory under certain circumstances, especially in the case of low concentrations of active compound and when low amounts are applied.

New phosphoric acid esters of the formula (I)

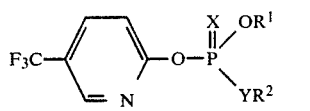

in which
  Y represents oxygen, sulphur or a —NR— group, wherein
  R represents hydrogen or alkyl,
  X represents oxygen or sulphur and
  $R^1$ and $R^2$ are identical or different and represent alkyl,
have now been found.

The new phosphoric acid esters of the formula (I) are obtained by a process in which 2-hydroxy-5-trifluoromethyl-pyridine of the formula (II)

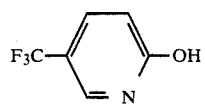

or the corresponding alkali metal, alkaline earth metal or ammonium salts, are reacted with halides of the formula (III)

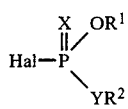

in which
  $R^1$, $R^2$, X and Y have the abovementioned meanings and
  Hal represents halogen (preferably chlorine or bromine),
if appropriate in the presence of an acid acceptor and if appropriate in the presence of a diluent.

The new phosphoric acid esters of the formula (I) are distinguished by a high activity as agents for combating pests, in particular by their outstanding insecticidal and nematicidal action.

The alkyl radicals R, $R^1$ and $R^2$ can be branched or straight-chain and preferably contain 1 to 8, in particular 1 to 6 and particularly preferably 1 to 4, carbon atoms. Examples which may be mentioned are: methyl, ethyl, n-propyl, i-propyl, n-butyl, i-butyl, sec.-butyl and tert.-butyl.

X preferably represents sulphur.

The invention preferably relates to compounds of the formula (I) in which
  Y represents oxygen, sulphur or a —NR— group, wherein
  R represents hydrogen or alkyl with 1 to 4 carbon atoms,
  X represents oxygen or sulphur and
  $R^1$ and $R^2$ are identical or different and represent alkyl with 1 to 6 carbon atoms.

Very particularly preferred compounds of the formula (I) are those in which
  Y represents oxygen, sulphur or a —NR— group, wherein
  R represents hydrogen, methyl or ethyl,
  X represents oxygen or sulphur and
  $R^1$ and $R^2$ are identical or different and represent methyl, ethyl, n-propyl, i-propyl, n-butyl, i-butyl, sec.-butyl or tert.-butyl.

Compounds of the formula (I) in which
  Y represents oxygen, sulphur or a —NR— group, wherein
  R represents hydrogen,
  X represents sulphur and
  $R^1$ and $R^2$ are identical or different and represent methyl, ethyl or n-propyl,
are distinguished by a particularly favourable activity.

If, for example, 2-hydroxy-5-trifluoromethylpyridine and O-ethyl S-n-propyl dithiophosphate-chloride are used as starting substances for the process according to the invention, the corresponding reaction can be outlined by the following equation:

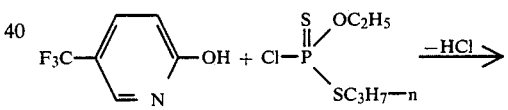

Formula (II) provides a definition of 2-hydroxy-5trifluoromethylpyridine and the corresponding salts. The alkali metal, alkaline earth metal or ammonium ions preferably represent sodium, potassium, calcium or ammonium ions.

Examples which may be mentioned of the starting substances of the formula (II) are: the sodium, potassium, calcium and ammonium salts of 2-hydroxy-5-trifluoromethylpyridine.

The compounds of the formula (II) are known compounds of organic chemistry.

Formula (III) provides a definition of the halides which are likewise to be employed as starting substances. In this formula, $R^1$, $R^2$, X and Y preferably represent those radicals which have been mentioned in the definition in formula (I). Hal in this formula preferably represents chlorine or bromine.

Examples which may be mentioned of the starting substances of the formula (III) are: dimethoxy-, diethoxy-, di-n-propoxy-, di-i-propoxy-, di-n-butoxy-, di-i-butoxy-, methoxy-ethoxy-, methoxy-n-propoxy-, methoxy-i-propoxy-, methoxy-n-butoxy-, methoxy-i-butoxy-, methoxy-sec.-butoxy-, methoxy-tert.-butoxy, ethoxy-n-propoxy-, ethoxy-i-propoxy, ethoxy-n-butoxy-, ethoxy-i-butoxy-, ethoxy-sec.-butoxy-, ethoxy-tert.-butoxy-, n-propoxy-i-propoxy-, n-propoxy-n-butoxy-, n-propoxy-i-butoxy-, n-propoxy-sec.-butoxy-, n-propoxy-tert.-butoxy-, i-propoxy-n-butoxy-, i-propoxy-i-butoxy-, n-butoxy-i-butoxy-, n-butoxy-sec.-butoxy- and n-butoxy-tert.-butoxy-(thiono)-phosphoric acid ester-chloride and -bromide; methoxymethylthio-, methoxy-ethylthio-, methoxy-n-propylthio-, methoxy-i-propylthio-, methoxy-n-butylthio-, methoxy-i-butylthio-, ethoxy-methylthio-, ethoxy-ethylthio-, ethoxy-n-propylthio-, ethoxy-i-propylthio-, ethoxy-n-butylthio-, ethoxy-i-butylthio-, ethoxy-sec.-butylthio-, n-propoxy-methylthio-, n-propoxy-ethylthio-, n-proxy-n-propylthio-, n-propoxy-i-propylthio-, n-propoxy-n-butylthio-, n-propoxy-i-butylthio-, i-propoxy-methylthio-, i-propoxy-ethylthio-, i-propoxy-n-propylthio-, i-propoxy-i-propylthio-, i-propoxy-n-butylthio-, i-propoxy-i-butylthio-, n-butoxy-methylthio-, n-butoxy-ethylthio-, n-butoxy-n-propylthio-, n-butoxy-i-propylthio-, n-butoxy-n-butylthio-, n-butoxy-i-butylthio-, i-butoxy-methylthio-, i-butoxy-ethylthio-, i-butoxy-n-propylthio-, i-butoxy-i-propylthio-, i-butoxy-n-butylthio- and i-butoxy-i-butylthio-(thiono)phosphoric acid ester-chloride and -bromide; methoxy-(di)methylamino-, methoxy-(di)ethylamino-, methoxy-(di)n-propylamino-, methoxy-(di)i-propylamino-, methoxy-(di)n-butylamino-, methoxy-(di)i-butylamino-, ethoxy-(di)methylamino-, ethoxy-(di)n-propylamino, ethoxy-(di)i-propylamino-, ethoxy-(di)n-butylamino-, ethoxy-(di)i-butylamino-, n-propoxy-(di)methylamino-, n-propoxy-(di)ethylamino-, n-propoxy-(di)n-propylamino-, n-propoxy-(di)i-propylamino-, n-propoxy-(di)n-butylamino-, n-propoxy-(di)i-butylamino-, i-propoxy-(di)methylamino-, i-propoxy-(di)ethylamino-, i-propoxy-(di)n-propylamino-, i-propoxy-(di)i-propylamino-, i-propoxy-(di)n-butylamino-, i-propoxy-(di)i-butylamino-, n-butoxy-(di)methylamino-, n-butoxy-(di)ethylamino-, n-butoxy-(di)n-propylamino-, n-butoxy-(di)i-propylamino-, n-butoxy-(di)n-butylamino-, n-butoxy-(di)i-butylamino-, i-butoxy-(di)methylamino-, i-butoxy-(di)ethylamino-, i-butoxy-(di)n-propylamino-, i-butoxy-(di)i-propylamino-, i-butoxy-(di)n-butylamino-, i-butoxy-(di)i-butylamino-, sec.-butoxy-(di)methylamino-, sec.-butoxy-(di)ethylamino-, sec.-butoxy-(di)n-propylamino-, sec.-butoxy-(di)i-propylamino-, sec.-butoxy-(di)-i-butylamino-, tert.-butoxy-(di)methylamino-, tert.-butoxy-(di)ethylamino-, tert.-butoxy-(di)n-propylamino- and tert.-butoxy-(di)n-butylamino-(thiono)phosphoric acid ester-chloride and -bromide.

The compounds of the formula (III) are known and/or can be prepared by generally known processes and methods (compare, for example, Methoden der organischen Chemie (Methods of organic chemistry) (Houben-Weyl-Müller), 4th edition, Volume 12/1 (1963), pages 415–420 and pages 560–563; Volume 12/2 (1964), pages 274–292, pages 405–408 and pages 607–618, pages 621–622 and pages 755–757; Thieme Verlag Stuttgart).

The process according to the invention for the preparation of the new phosphoric acid esters of the formula (I) is preferably carried out using diluents. Possible diluents are virtually all the inert organic solvents.

These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylene sulphone and hexamethylphosphoric acid triamide.

If appropriate, the process can be carried out in the presence of acid acceptors. All the customary acid-binding agents can be used as acid acceptors. Acid acceptors which have proved particularly suitable are alkali metal carbonates and alcoholates, such as sodium carbonate, potassium carbonate, sodium methylate and ethylate and potassium methylate and ethylate, and furthermore aliphatic, aromatic or heterocyclic amines, for example triethylamine, trimethylamine, dimethylaniline, dimethylbenzylamine and pyridine.

The process according to the invention is in general carried out at temperatures between 0° C. and 120° C. The range between 20° C. and 100° C. is preferred. The reactions are in general carried out under normal pressure.

For carrying out the process according to the invention, the starting substances (II) and (III) are usually employed in approximately equimolar amounts. An excess of either of the reaction components provides no substantial advantages.

The reactions are in general carried out in a suitable diluent and, if appropriate, in the presence of an acid acceptor.

The compounds obtainable according to the invention are worked up by customary methods. The new compounds are in some cases obtained in the form of oils, some of which cannot be distilled without decomposition, but can be freed from the last volatile constituents by so-called "incipient distillation", that is to say by prolonged heating to moderately elevated temperatures under reduced pressure, and can in this way be purified. They are characterized by their refractive index.

The active compounds are well tolerated by plants, have a favorable level of toxicity to warmblooded animals, and are suitable for combating animal pests, especially insects and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella*

*germanica, Acheta demosticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex Lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma Lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata Lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrylsorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Dabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psyllpides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.*

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The good action against nematodes and soil insects is to be particularly emphasized, and a good systemic action, in particular a root-systemic action, is furthermore to be observed.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation of the compounds according to the invention is illustrated by the following preparation examples:

EXAMPLE 1

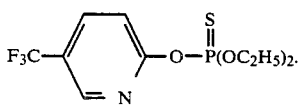

F$_3$C—〈pyridine〉—O—P(OC$_2$H$_5$)$_2$, S 9.4 g (0.05 mole) of O,O-diethyl thionpphosphate-chloride were added dropwise to a suspension of 8.2 g (0.05 mole) of 2-hydroxy-5-trifluoromethylpyridine and 8 g (0.058 mole) of potassium carbonate in 80 ml of acetonitrile at 20° C. The mixture was then stirred at 70° C. for 2 hours, cooled and filtered. The filtrate was concentrated and the residue was subjected to incipient distillation. 15 g (96% of theory) of O,O-diethyl O-(5-trifluoromethylpyrid-2-yl)thionophosphate were obtained in the form of a yellow oil with a refractive index $n^{22}$ of 1.4718.

The following compounds of the formula (I) were prepared analogously to Example (1):

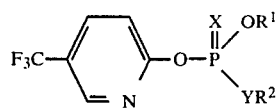

| Example No. | X | Y | R$^1$ | R$^2$ | Refractive Index |
|---|---|---|---|---|---|
| 2 | S | S | C$_2$H$_5$ | n-C$_3$H$_7$ | $n_D^{22}$ = 1.5111 |
| 3 | S | NH | C$_2$H$_5$ | CH$_3$ | $n_D^{22}$ = 1.5004 |
| 4 | O | S | C$_2$H$_5$ | n-C$_3$H$_7$ | Oil |

-continued

| Example No. | X | Y | R$^1$ | R$^2$ | Refractive Index |
|---|---|---|---|---|---|
| 5 | S | O | C$_2$H$_5$ | i-C$_3$H$_7$ | $n_D^{22}$ = 1.4701 |

EXAMPLE A

LT$_{100}$ test for Diptera
Test insects: *Musca domestica* (resistant)
Solvent: Acetone 2 parts by weight of active compound are taken up in 1,000 parts by volume of solvent. The solution thus obtained is diluted with further solvent to the desired lower concentration.

2.5 ml of the active compound solution are pipetted into a Petri dish. A filterpaper disc of 9.5 cm diameter is located on the bottom of the Petri dish. The Petri dish is left standing open until the solvent has completely evaporated. The amount of active compound per m$^2$ of filterpaper varies, depending on the concentration of the active compound solution. About 25 test insects are then introduced into the Petri dish, and the dish is covered with a glass lid.

The condition of the test insects is checked continuously. The time required for a 100% knock-down effect is determined.

In this test, for example, the compound of preparation Example (1) showed a 100% action after 210 minutes, at an active compound concentration of 0.002%.

EXAMPLE B

Drosophila test
Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

1 cm$^3$ of the preparation of the active compound is pipetted onto a filter paper disc (7 cm diameter). The wet disc is placed over the opening of a glass vessel containing 50 vinegar flies (*Drosophila melanogaster*) and is covered with a glass plate.

After the specified periods of time, the destruction in % is determined. 100% means that all the flies have been killed; 0% means that none of the flies have been killed.

In this test, for example, the compound of preparation Example (1) showed a degree of destruction of 100% after 1 day, at an active compound concentration of 0.001%.

EXAMPLE C

Plutella test
Solvent: 3 parts by weight of acetone
Emulsifier: 1 part by weight of alkylaryl polyglycol ether To produce a suitable preparation of active compound, 1 part by weight of active compound is mixed with the stated amount of solvent the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, for example, the compound of preparation Example (1) showed a degree of destruction of 100% after 3 days, at an active compound concentration of 0.01%.

EXAMPLE D

Test insect: *Phorbia antiqua* grubs in the soil
Solvent: 3 parts by weight of acetone
Emulsifer: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of preparation Examples (1), (2) and (3) showed a degree of destruction of 100%, at an active compound concentration of 20 ppm.

EXAMPLE E

Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead insects. The root-systemic action of the active compound is deduced from the mortality figures. It is 100% if all the test insects have been killed and 0% if just as many test insects are still alive as in the case of the untreated control.

In this test, for example, the compounds of preparation Examples (1) and (3) showed a degree of destruction of 95% and 100% respectively, at an active compound concentration of 20 ppm.

EXAMPLE F

Test Nematode: *Meloidogyne incognita*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, lettuce is sown in and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds of preparation Examples (1), (2) and (3) showed a degree of destruction of 100%, at an active compound concentration of 20 ppm.

EXAMPLE G

Test nematode: *Globodera rostochiensis*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, potatoes are planted and the pots are kept at a greenhouse temperature of 18° C.

After six weeks, the potato roots are examined for cysts and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds of preparation Examples (1), (2) and (3) showed a degree of destruction of 100%, at an active compound concentration of 20 ppm.

It will be understood that the specification and examples are illustrative but not limitative of the present invention and that other embodiments within the spirit and scope of the invention will suggest themselves to those skilled in the art.

What is claimed is:

1. A phosphoric acid ester of the formula

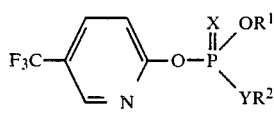

in which
Y is oxygen or sulphur or —NH—,
X is oxygen or sulphur, and
$R^1$ and $R^2$ each independently is alkyl with 1 to 6 carbon atoms.

2. A compound according to claim 1, in which $R^1$ and $R^2$ each independently is methyl, ethyl, n-propyl, i-propyl, n-butyl, i-butyl, sec.-butyl or tert.-butyl.

3. A compound according to claim 1, in which X is sulphur, and $R^1$ and $R^2$ each independently is methyl, ethyl or n-propyl.

4. A compound according to claim 1, wherein such compound is O,O-diethyl O-(5-trifluoromethylpyrid-2-yl)thionophosphate of the formula

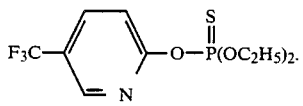

5. A compound according to claim 1, wherein such compound is O-ethyl S-n-propyl-O-(5-trimethylfluoromethylpyrid-2-yl)thionothiolphosphate of the formula

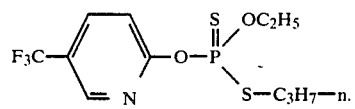

6. A compound according to claim 1, wherein such compound is O-ethyl N-methyl O-(5-trimethylfluoromethylpyrid-2-yl)thionophosphoric acid esteramide of the formula

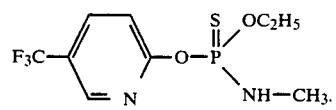

7. A compound according to claim 1, wherein such compound is O-ethyl S-n-propyl-O(5-trimethylfluoromethylpyrid-2-yl)thiolphosphate of the formula

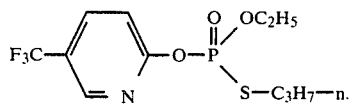

8. A compound according to claim 1, wherein such compound is O-ethyl O-isopropyl O-(5-trimethylfluoromethylpyrid-2-yl)thionophosphate of the formula

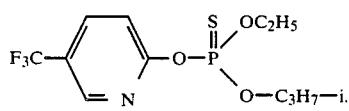

9. An insecticidal or nematicidal composition comprising an insecticidally or nematicidally effective amount of a compound according to claim 1 in admixture with a diluent.

10. A method of combating insects or nematodes which comprises applying to such insects or nematodes or to a habitat thereof an insecticidally or nematicidally effective amount of a compound according to claim 1.

11. The method according to claim 10, wherein such compound is

O,O-diethyl O-(5-trifluoromethylpyrid-2-yl) thionophosphate,
O-ethyl S-n-propyl-O-(5-trimethylfluoromethylpyrid-2-yl)thionothiolphosphate,
O-ethyl N-methyl O-(5-trimethylfluoromethylpyrid-2-yl)thionophosphoric acid esteramide,
O-ethyl S-n-propyl-O-(5-trimethylfluoromethylpyrid-2-yl)thiolphosphate, or
O-ethyl O-isopropyl O-(5-trimethylfluoromethylpyrid-2-yl)thionophosphate.

* * * * *